United States Patent [19]

Melnick et al.

[11] 4,263,405
[45] Apr. 21, 1981

[54] APPARATUS FOR MEASURING THE APPROXIMATE NUMBER OF AEROBIC BACTERIA IN WATER AND OTHER FLUIDS

[75] Inventors: Joseph L. Melnick; Craig Wallis, both of Houston, Tex.

[73] Assignee: Baylor College of Medicine, Houston, Tex.

[21] Appl. No.: 57,237

[22] Filed: Jul. 13, 1979

Related U.S. Application Data

[63] Continuation-in-part of Ser. No. 959,115, Nov. 9, 1978, which is a continuation-in-part of Ser. No. 776,323, Mar. 10, 1977, abandoned.

[51] Int. Cl.³ .............................................. C12M 1/34
[52] U.S. Cl. ................................. 435/291; 73/432 R; 422/59; 435/287; 435/296; 435/299; 435/300; 435/807

[58] Field of Search ............... 73/16, 426, 432 R, 747; 435/291, 287, 296, 299, 300, 317, 807; 422/58, 59, 102

[56] References Cited

U.S. PATENT DOCUMENTS

| | | | |
|---|---|---|---|
| 1,046,259 | 12/1912 | Bunzel | 435/291 X |
| 2,019,950 | 11/1935 | Bunzel | 435/807 X |
| 2,321,293 | 6/1943 | Hassler | 435/291 X |
| 3,182,497 | 5/1965 | Rubens et al. | 73/16 X |

Primary Examiner—Robert J. Warden
Attorney, Agent, or Firm—Louis E. Marn; Elliot M. Olstein

[57] ABSTRACT

A simple and functional apparatus is disclosed for use in the home, field and other places in which water or other fluids can be evaluated for the presence of bacteria. Also disclosed is a convenient tablet reagent for use with liquid peroxide with the apparatus.

6 Claims, 9 Drawing Figures

APPARATUS FOR MEASURING THE APPROXIMATE NUMBER OF AEROBIC BACTERIA IN WATER AND OTHER FLUIDS

CROSS-REFERENCE TO RELATED APPLICATION

This application is a Continuation-In-Part of application Ser. No. 959,115, filed on Nov. 9, 1978, which is a continuation-in-part of Ser. No. 776,323, filed Mar. 10, 1977 and now abandoned.

BACKGROUND OF THE INVENTION

In our application, Ser. No. 959,115, filed on Nov. 9, 1978, we disclosed a method and apparatus for the accurate quantification of aerobic bacteria (catalase-containing organisms) in fluids by reacting hydrogen peroxide with the bacteria in a sealed container under controlled conditions which require a void space of 20-40%, a contact time (incubation) between the reactants (bacteria and peroxide) of about 5-30 minutes or longer, and that, before measuring the pressure generated by the catalysis of peroxide by bacterial enzymes into water and gaseous oxygen ($O_2 \uparrow$), the vessel is vigorously shaken or the fluids are vigorously agitated to release the aqueous phase oxygen into the void space of the container. The sealed container is connected to a transducer or a manometer, by which the amount of pressure generated is measured as psi (transducer) or by the height of the fluids (manometer). By relating these results to a known standard nomograph developed experimentally, the approximate number of bacteria is determined.

The above technology lends itself to laboratories where the proper equipment is available. Extension of this technology to field and industry conditions where bacteria can be detected and quantified in many liquids, for example water used for drinking, swimming pools, cooling towers, cutting oils, milk and the like by the consumer requires a practical device or apparatus as described in this application. Therefore, this application is concerned with a simple and functional apparatus for use in the home, field, industrial, and other places where water or other fluids can be evaluated for the presence of bacteria. Furthermore, this application is discloses reagents in single tablet form for use with liquid peroxide with this apparatus thereby avoiding the cumbersome task of using all individual liquid agents which require excess reagent bottles and droppers.

SUMMARY OF THE INVENTION

The present invention is directed to an apparatus which comprises a closed reaction vessel having an open end closed by an adjustable and removable closure, such as a threaded cap for closing the vessel. A manometer is provided on the body of the vessel, and is in fluid communication with the inside of the vessel adjacent the open end. The manometer opens to the atmosphere at its upper end.

Suitable indicia is provided on the vessel to indicate the approximate number of bacteria present based on the level of fluid driven from the inside of the vessel into the manometer. Preferably, and for practical purposes, the manometer is color coded to indicate the various amounts of bacteria present. An O-ring or other sealing means is provided in connection with the removable closure to form a seal with the vessel. The closure is adjustable for zeroing the height of the fluid in the manometer.

The present invention is also directed to a tablet combining the reagents for use along with peroxide with the vessel rather than requiring the cumbersome task of adding individual agents in liquid form to the test fluids. The tablet includes a chelator, a reducing agent, and a dye, and, when added to the test fluids, with liquid peroxide, effects the same end results when using the individual agents added in liquid form.

It is therefore an object of the present invention to provide a simple and functional apparatus for use in the home, field, in industry, and other places where water or other fluids can be evaluated for the presence of bacteria easily and readily.

A further object of the present invention is the provision of a relatively simple and functional apparatus including a reaction vessel having a manometer that quantifies oxygen based on the pressure produced by the generated gas as it compresses water or other fluids and drives these fluids up the manometer.

Other and further objects, features and advantages appear throughout.

DESCRIPTION OF THE PREFERRED EMBODIMENTS

Figure 1:
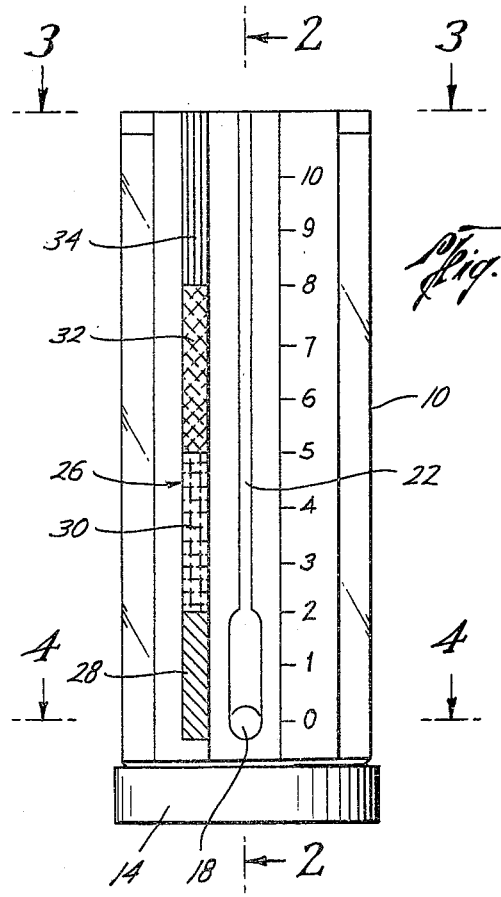
FIG. 1 is a side elevational view of the reaction vessel according to the drawing including color coding parallel to the manometer to indicate the approximate number of bacteria present, based on the level of fluid driven from the inside of the vessel into the manometer, in the test fluid.
Figure 2:
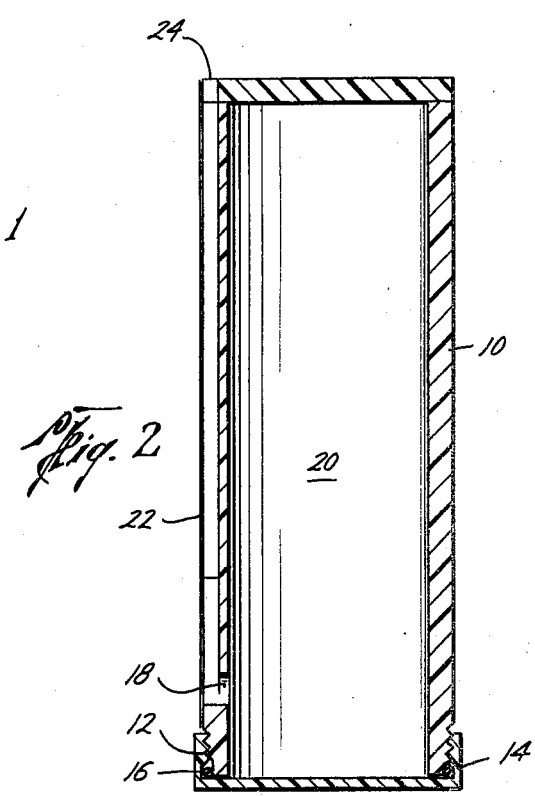
FIG. 2 is a longitudinal sectional view taken along the line 2—2 of FIG. 1.
Figure 3:
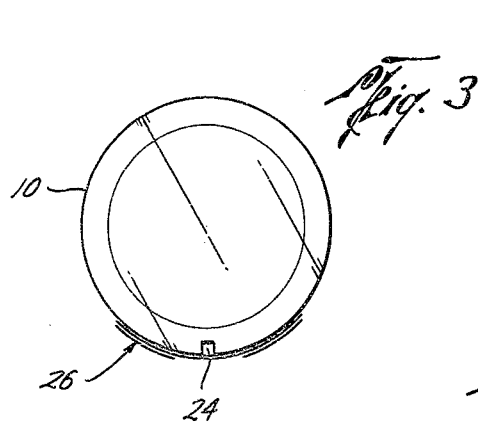
FIG. 3 is a cross-sectional view taken along the line 3—3 of FIG. 1.
Figure 4:
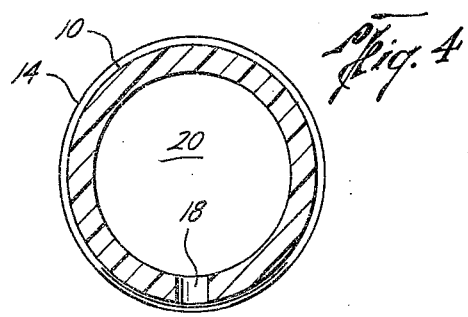
FIG. 4 is a cross-sectional view taken along the line 4—4 of FIG. 1.

A presently preferred reaction vessel 10 is illustrated in FIGS. 1-4 and 6-10. Preferably, it is a 100-ml capacity plastic vessel with the threads 12 on one end for threadly receiving the threaded cap 14 to close the pressure vessel 10. Suitable sealing means, such as the O-ring 16 are provided.

The reaction vessel 10 as illustrated in the drawings is tapered slightly, but this is for manufacturing purposes for injection molding, and the taper configuration plays no role in the function of the apparatus.

The vessel can be formed of any inert, rigid material, such as the thermal and thermosetting plastics, plexiglass, and the like. It can be transparent to opaque. Preferably, the material is one that can be molded by injection molding, such as polypropylene.

Proximal to the threaded end 12 of the reaction vessel 10 is an opening 18 which leads from the inside 20 of the reaction vessel 10 to a manometer 22 which is machined or molded onto the outside of the vessel 10. As here shown, the manometer 22 is a ¼-inch diameter tube which is open to the atmosphere at its upper end 24. Thus, fluid communication is provided between the interior 20 of the reaction vessel 10 and the manometer 22. As described in more detail later, the manometer becomes partially filled to a normal fluid level at the time the test is initiated, which is a normal fluid level in the case of test waters which have insufficient bacteria to produce positive pressure by decomposing peroxide.

For ease of indicating the amount of bacteria present in the test fluids, the manometer 22 is color coded, such as by the strip 26 paralleling it to indicate the approximate number of bacteria present based on the level of fluid driven from the inside 20 of the reaction vessel 10 into the manometer 22. At the baseline reservoir, the color is green, as indicated at 28, which indicates less than 10,000 bacteria/ml, which is the sensitivity of this reaction vessel. Above the baseline reservoir and for 1½-inches higher is a yellow zone, indicated by the reference numeral 30, indicative of about 10,000–30,000 bacteria/ml. Above the yellow zone 30 is an orange zone, indicated by the reference numeral 32, indicating about 50,000 (between 30,000 and 70,000) bacteria/ml. And above this zone is the red zone 34 which indicates an excess of bacteria, that is 100,000 or greater bacteria/ml.

The cap 14 can be a plastic or Bakelite screw cap for sealing the vessel. Also, by adjusting or rotating the cap 14 counterclockwise, the level of fluid in the manometer can be set to zero. Any quick connecting closure can be used which is adjustable or has an adjustable member by which the test fluid can be set to zero in the manometer 22.

Water level marks are provided by the column of numbers paralleling the manometer 22 on the right side of the vessel or, if desired, a separate water level mark could be provided. In this case, however, the water level mark is provided by the horizontally-extending line opposite the number 2 on this column of numbers.

The size of the vessel described and illustrated is not necessarily the required size. Any sized vessel can be used, as long as the device is equipped with a manometer which is fed from the inside of the vessel and includes adjustable means to zero the test fluid in the manometer.

Figure 5:
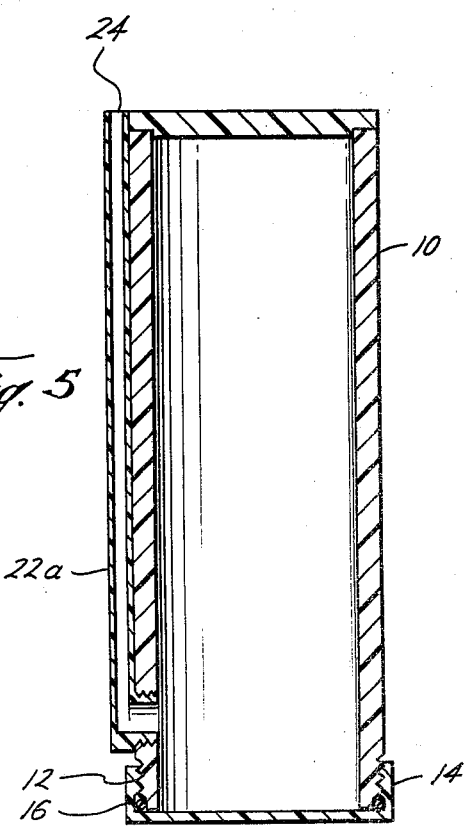
FIG. 5 is a view similar to that of FIG. 2 illustrating a modification.

If desired, a separate manometer 22a can be secured to the outer wall of the vessel 10, such as illustrated in FIG. 5, rather than the grooved or machined manometer 22 in the outer wall of the vessel 10, such as illustrated in FIGS. 1–4.

If desired, however, the manometer need not be engraved, machined or molded into the body or applied to the body of the vessel, but can be a separate part of the vessel, for example, a tube leading from the inside of the vessel and bent against the side of the vessel.

Advantageously, the reagents for use with liquid peroxide in the apparatus or reaction vessel 10 can be in a single tablet form. This would include a chelating agent, a reducing agent, and a dye. The addition of these reagents separately is a cumbersome task and requires excess reagent bottles and droppers. The operation of the test is improved, we have found, by utilizing a single tablet which when added with liquid peroxide to the test fluids, in the vessel 10 effect the same end results as when adding the individual agents in liquid form.

Preferably, the tablet is composed of sodium thiosulfate, or other reducing agent, citric acid and methylene blue (or other suitable dye). The thiosulfate, citric acid powder and dye powder are all milled to a homogenous consistency and at proportions that, when tableted with a filler, preferably yield a final product of 0.01 M sodium citrate (a chelator), 5 ppm thiosulfate, and 0.01% methylene blue by weight when dissolved in 80 ml of test fluids. The concentrations of the above powders can be varied as hereinafter set forth and any desired final concentrations of the three reagents can be obtained. However, the formula described above appears to be ideal with 0.3% liquid peroxide for use with this device under the conditions described above. Any suitable commercial filler can be used, such as talcum powder and the like.

Figure 6:
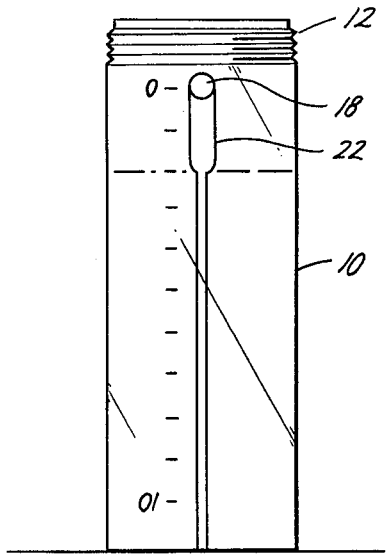
FIG. 6 is an elevational view of the vessel of FIG. 1 illustrating the position of the vessel when filling with the test fluid and showing the height of the fluid therein.
Figure 7:
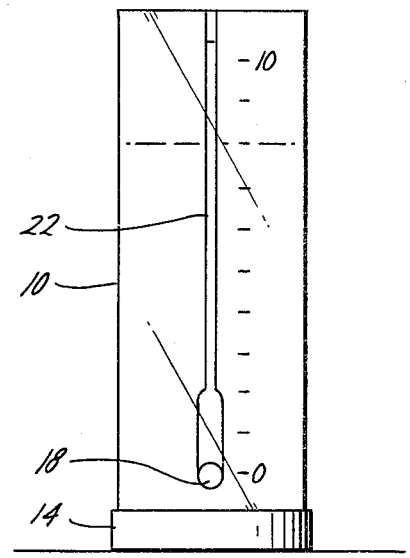
FIG. 7 is a view similar to that of FIG. 6 but illustrates the vessel with the cap threaded into position and the vessel inverted.

Test fluids such as potable water (such as drinking water), homogenized milk, water from a humidifier, or cooling tower, swimming pools, cutting oils or the like are added to the reaction vessel 10, as illustrated in FIG. 6, with the cap 14 removed until the test fluids reach the "water level" mark. As illustrated in FIG. 6, this water level mark is 80 ml (80% by volume) and appears to be the optimal volume for this size vessel to obtain the most sensitivity; although 60 to 90% by volume can be used. The reaction vessel 10 is allowed to stand at room or ambient temperature (based on the location of the test) to allow the test fluids to equilibrate with the environmental temperature. Liquid peroxide and the tablet described above are then added or, if desired, the reagents can be added separately. In the latter case, peroxide is added to the water to obtain a final concentration of from about 0.1% to about 2.25% by weight, preferably for this reaction vessel 10 about 0.3% by weight. A chelating agent is added to bind heavy metals that interfere with peroxide, and this concentration can be 0.1–0.0001 M. Sodium thiosulfate or another reducing agent is added to bind chlorine if it is present at 0.5 to 10.0 ppm thiosulfate. And, lastly, a dye is added to give color to the water so that the rise of fluid from the vessel up the manometer 22 is easily discerned, for example, from about 0.1% to about 0.01% by weight of the test fluids. All but the peroxide can be added in the form of a single tablet. The cap 14 is then placed on the vessel thereby sealing it and the vessel is inverted, as illustrated in FIG. 7, and allowed to stand on a flat surface with the cap 14 down on this surface for an incubation period of about 15 minutes optimally, but longer if desired.

Figure 8:
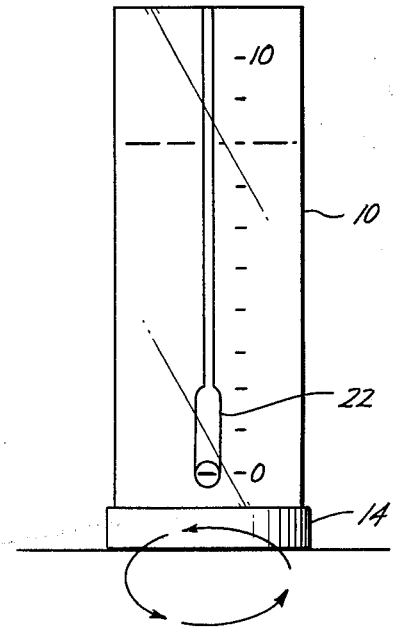
FIG. 8 is a view similar to that of FIG. 7 and illustrates adjustment of the cap for sealing in the test fluids to approximately 80% of the volume of the reaction vessel.
Figure 9:
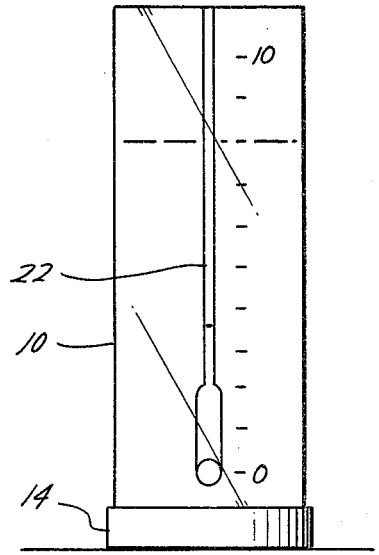
FIG. 9 is a view similar to that of FIG. 8 illustrating the height of test fluid in the manometer after the test fluid has been incubated for the required amount of time and has been agitated by vigorously shaking the vessel.

At the time of the above inversion, the reaction vessel 10 is shaken with the finger over the manometer outlet 24 to release excess oxygen which may be present in the test water and the vessel is then placed on the flat surface. After the above 15 minute incubation period, the manometer fluid is set to zero by turning the screw cap 14 counterclockwise so that the fluid in the manometer 22 is at zero, as shown in FIG. 8. Once at zero the reaction vessel 10 is vigorously shaken a few times with one finger over the top of the effluent opening 24 of the manometer 22. The test vessel 10 is then placed on a flat surface with the cap 14 down, as illustrated in FIG. 9, and the manometer is read. If there are bacteria in the test fluids adequate in number to catalytically convert peroxide into water and $O_2 \uparrow$, the end result will indicate the concentration of bacteria. For example, if the fluid in the manometer 22 rises above the baseline, bacteria are present in excess of 10,000/ml. Based on the height of the fluid in the manometer 22, the bacterial numbers can be quantitatively determined.

It should be noted that when the cap 14 is placed on the reaction vessel 10, positive pressure will naturally be exerted into the vessel. However, since the manometer or opening 18 leading from the interior 20 of the reaction vessel 10 into the manometer 22 is above the test fluid level at the time of closing the vessel, the pressure induced dissipates through the manometer and the pressure inside the vessel will have equilibrated with the atmosphere.

The following examples are representative examples of the use of this reaction vessel and reagent.

EXAMPLE 1

Drinking water obtained from a tap was added to the reaction vessel 10 as described above as shown in FIG. 6 to the "water mark", 80% of the volume of the reaction vessel 10. One reagent tablet and liquid peroxide as described above were added, and the device was rotated gently to dissolve the tablet. A sample of the drinking water was also obtained for plating on agar plates to determine the bacterial CFU/ml. After the tablet dissolved (30 seconds), the device was capped with the cap 12, inverted, as illustrated in FIG. 7, and allowed to stand at room temperature for 15 minutes (with the cap side of the vessel on the surface of the table). The cap 14 was rotated to zero the fluid level in the manometer. After 15 minutes, the reaction vessel 10 was shaken vigorously, placed on the table, and the manometer read. The test fluids remained in the baseline reservoir, indicating less than 10,000 CFU/ml bacteria. The assay of the drinking water on agar plates was enumerated for bacteria after a 48 hour incubation and manifested only 250 CFU/ml, confirming the results evidenced by the device at the time of the test.

A duplicate sample of the same water was seeded with *Pseudomonas aeruginosa*, and an aliquot was assayed on agar described above. After a 15 minute holding time and vigorous shaking, the manometer manifested test fluids in the lower part of the yellow zone, indicating approximately 12,000 CFU/ml. The bacterial assays enumerated after 48 hours incubation showed a titer of 14,000 CFU/ml, confirming the results of the device.

EXAMPLE 2

Drinking water from a tap that contained an upstream water naturalizer (charcoal filter), which is known to concentrate organics from water and provide a breeding ground for bacterial growth (Wallis, Stagg and Melnick, Water Research 8:111-113, 1974), was tested by obtaining the first morning flush from the tap. The test vessel 10 was loaded, treated with the reagent tablet, peroxide, capped, and after the 15 minute incubation time, vigorously shaken, as described in Example 1. The manometer reading indicated fluid in the red color zone. This indicated an excess of bacteria, in the range of 100,000 CFU/ml. Plating of a representative sample of this first flush indicated 130,000 bacteria/ml.

EXAMPLE 3

Homogenized milk purchased at a supermarket was tested in the test vessel 10 as described in Example 1. The manometric reading was in the baseline zone, indicating less than 10,000 CFU/ml. Plating of a representative sample at the time of the test manifested only 700 CFU/ml 48 hours after plating, again confirming the efficiency of the device. However, another sample of milk obtained from another market gave a positive test, with the milk rising to the orange zone in the manometer, manifesting about 50,000 bacteria/ml. Plating confirmed these results, as the assay yielded 46,000 CFU/ml. The importance of this latter test is indicated by the fact that milk contains a lacto-peroxidase that is capable of decomposing peroxide to water and an acceptor oxygen which is not a gaseous oxygen producing positive pressure. Thus, even in the presence of this peroxidase, there is sufficient peroxide in our system to efficiently quantify bacterial catalase.

EXAMPLE 4

A humidifier that is used to humidify room air and contains a water reservoir (known to promote growth of bacteria and present a health hazard) was tested by obtaining the humidifier reservoir's fluids and tested as described in Example 1. The results with the device indicated excess pressure since the test fluids filled the manometer and overflowed through the effluent opening of the manometer. Plating of the sample indicated 175,000 CFU/ml.

EXAMPLE 5

Cutting oils, which are used in machinery plants and which support the growth of bacteria, were tested as described in Example 1. The results of the test with the device gave a manometer reading in the orange zone, indicating about 75,000 bacteria/ml. The plating of the cutting oil also gave a similar count, i.e., 71,000 CFU/ml.

EXAMPLE 6

Water from a private swimming pool was tested as described in Example 1. The manometer reading was in the green zone, and the plating of the pool water also indicated only 1500 bacteria/ml. A second pool tested gave a positive reading in the yellow zone, and plating indicated 14,000 CFU/ml.

Although reagent tablets were used in the foregoing examples, the conventional use of liquid reagents as described above and in our related application attained the same end results as the use of the single reagent tablets. Also, good results are obtained by filling the reaction vessel 10 to a "water mark" of from "1" to "4" on the numbers alongside the manometer 22, thus filling 60% to 90% by volume of the reaction vessel 10 with test fluids thus leaving a void space of 10-40%.

The present invention therefore is well suited and adapted to attain the objects and ends described and has the advantages and features mentioned as well as others inherent therein.

While presently preferred embodiments of the invention have been given for the purpose of disclosure, changes can be made therein which are within the spirit of the invention as defined by the scope of the appended claims.

What is claimed is:

1. Apparatus for measuring bacteria in a test fluid, comprising:
   a closed vessel having a bottom, a top and an opening adjacent said top, said vessel including an indicia for test fluid level located to provide a test fluid level in the vessel of from 60% to 90% of the volume of the vessel measured from the bottom thereof;

a manometer in fluid communication with the vessel interior adjacent the top thereof and above the indicia of test fluid level and positioned to provide a pressure measurement by test fluid from the vessel when the vessel is in an inverted position; indicia for test fluid level in the manometer which includes a base level and levels above the base level corresponding to amounts of bacteria in a test fluid; and an adjustable closure means for closing the opening in the vessel and for adjusting test fluid level in the manometer to the base level prior to pressure measurement for bacteria determination, whereby upon addition of test fluid and reagents and inversion of the vessel, bacteria are measured by the change of level of fluid in the manometer resulting from fluid compression caused by gas release.

2. The apparatus of claim 1 wherein the opening is a threaded opening and the closure means is a screw cap.

3. The apparatus of claim 2 wherein the manometer is secured to the side of the vessel.

4. The apparatus of claim 2 wherein the manometer is machined into the side of the vessel.

5. The apparatus of claim 2 wherein the indicia for said manometer is a strip having color codes attached to the vessel adjacent and parallel to the manometer indicating approximate amounts of bacteria present in the test fluid.

6. The apparatus of claim 2 wherein the indicia for test fluid level in the vessel is located to provide a test fluid level of 80% of the volume of the vessel measured from the bottom thereof.

* * * * *